(12) United States Patent
Nichols et al.

(10) Patent No.: US 7,241,740 B2
(45) Date of Patent: Jul. 10, 2007

(54) PEPTIDES AS SOLUBILIZING EXCIPIENTS FOR TRANSFORMING GROWTH FACTOR BETA PROTEINS

(75) Inventors: Pilarin E.L. Nichols, Andover, MA (US); Bernardo Perez-Ramirez, Brookline, MA (US)

(73) Assignee: Wyeth, Madison, NJ (US)

( * ) Notice: Subject to any disclaimer, the term of this patent is extended or adjusted under 35 U.S.C. 154(b) by 618 days.

(21) Appl. No.: 10/639,396

(22) Filed: Aug. 12, 2003

(65) Prior Publication Data

US 2004/0102378 A1 May 27, 2004

Related U.S. Application Data

(60) Provisional application No. 60/402,733, filed on Aug. 13, 2002.

(51) Int. Cl.
| A61K 38/07 | (2006.01) |
| A61K 38/08 | (2006.01) |
| A61K 38/10 | (2006.01) |
| A61K 38/18 | (2006.01) |
| A61K 38/39 | (2006.01) |
| C07K 14/495 | (2006.01) |
| C07K 14/51 | (2006.01) |

(52) U.S. Cl. .............. 514/18; 514/12; 514/13; 514/14; 514/16; 514/801; 424/426; 530/326; 530/327; 530/329; 530/330; 530/350

(58) Field of Classification Search .......... None
See application file for complete search history.

(56) References Cited

U.S. PATENT DOCUMENTS

| 4,877,864 A | 10/1989 | Wang et al. ............ 514/12 |
| 5,013,649 A * | 5/1991 | Wang et al. ............ 435/69.1 |
| 5,106,748 A | 4/1992 | Wozney et al. .......... 435/252.3 |
| 5,108,922 A | 4/1992 | Wang et al. ............ 435/365.1 |
| 5,116,738 A | 5/1992 | Wang et al. ............ 435/69.1 |
| 5,141,905 A | 8/1992 | Rosen et al. ............ 435/69.1 |
| 5,187,076 A | 2/1993 | Wozney et al. .......... 435/69.1 |
| 5,413,914 A | 5/1995 | Franzusoff |
| 5,635,375 A | 6/1997 | Kraus et al. ............ 435/71.1 |
| 5,637,480 A | 6/1997 | Celeste et al. .......... 435/69.4 |
| 5,639,638 A | 6/1997 | Wozney et al. .......... 435/69.4 |
| 5,658,882 A | 8/1997 | Celeste et al. ............ 514/12 |
| 5,661,007 A | 8/1997 | Wozney et al. .......... 435/69.4 |
| 5,688,678 A | 11/1997 | Hewick et al. ............ 435/325 |
| 5,756,457 A * | 5/1998 | Wang et al. ............ 514/12 |
| 5,922,846 A | 7/1999 | Cerletti et al. |

OTHER PUBLICATIONS

Rathore et al. N-terminal isoforms of recombinant human bone morphogenetic protein (rhBMP-2) are active in vitro and in vivo. Protein Sci. 4[Suppl.2], 443S (1995).*
Groppe et al. Biochemical and biophysical characterization of refolded Drosophila DDP, a homolog of bone morphogenetic proteins 2 and 4. J Biol Chem. Oct. 30, 1998;273(44):290052-65.*
Ebendal et al. 1998, *J. Neurosci.* 51:139.
Reddi, 1998, *Nat. Biotechnol.* 16:247.
Wozney, 1989, *Prog. Growth Factor Res.* 1(1):267.
International Search Report for PCT/US03/25177, mailed Oct. 26, 2004.

* cited by examiner

*Primary Examiner*—David Romeo
(74) *Attorney, Agent, or Firm*—Finnegan, Henderson, Farabow, Garrett & Dunner LLP

(57) ABSTRACT

The present invention relates to compositions comprising excipients or solubilizing agents for proteins. The invention relates to the discovery that a peptide derived from the N-terminus extension of the T266 isoform of rhBMP-2 has properties that enhance the solubility of proteins. The invention also relates to methods of resolubilizing a protein that has precipitated, by contacting the protein with a peptide comprised of the 17 amino acid extension of the T266 isoform of rhBMP-2. The invention also relates to methods of increasing the solubility of a protein by contacting the protein with a peptide comprised of the 17 amino acid extension of the T266 isoform of rhBMP-2.

16 Claims, 5 Drawing Sheets ves. Protein members of the TGF-β superfamily influence

SEQUENCE LISTING

<160> NUMBER OF SEQ ID NOS: 2

<210> SEQ ID NO 1
<211> LENGTH: 17
<212> TYPE: PRT
<213> ORGANISM: Homo sapiens

<400> SEQUENCE: 1

Thr Phe Gly His Asp Gly Lys Gly His Pro Leu His Lys Arg Glu Lys
1               5                   10                  15

Arg

<210> SEQ ID NO 2

```
<211> LENGTH: 51
<212> TYPE: DNA
<213> ORGANISM: Homo sapiens

<400> SEQUENCE: 2
acgtttggcc acgacggcaa aggccacccc ctgcacaaaa gagagaaaag a          51
```

PEPTIDES AS SOLUBILIZING EXCIPIENTS FOR TRANSFORMING GROWTH FACTOR BETA PROTEINS This application claims priority to U.S. Provisional Application No. 60/402,733 filed Aug. 13, 2002.

FIELD OF THE INVENTION

The invention relates generally to excipients and agents which solubilize proteins. In particular, the invention relates to compositions for, and methods of, maintaining or increasing the solubility of a protein under various biochemical conditions. The invention also relates to methods of, and compositions for, resolubilizing a protein which has precipitated out of solution. In a particular aspect, the invention relates to compositions for, and methods of, maintaining or increasing the solubility of proteins that belong to the transforming growth factor-β (TGF-β) superfamily.

BACKGROUND OF THE INVENTION

The TGF-β superfamily consists of more than 25 different signaling proteins found in both vertebrates and invertebrates. Protein members of the TGF-β superfamily influence a wide range of biological processes including cell growth, cell growth inhibition, tissue repair, cell differentiation, apoptosis, establishment of the dorso-ventral embryo body axis, and secretion of extracellular matrix components (Ebendal et al. 1998, *Journal of Neuroscience* 51:139). Thus, members of the TGF-β superfamily provide attractive targets for the development of pharmaceutical agonists and antagonists that may be used to treat a wide variety of human diseases and conditions which are affected by the activity of one or more of the superfamily members. For example, antagonists and agonists of TGF-β superfamily members have practical application in the area of tissue repair and regeneration as well as in the area of differentiation of pluripotent stem cells into cells or tissues of a preferred lineage. Additionally, TGF-β superfamily members also provide targets for gene therapy. The cloning and expression of many members of the family has been described. (See e.g. U.S. Pat. Nos. 4,877,864; 5,108,922; 5,013,649; 5,116,738; 5,106,748; 5,187,076; 5,141,905; 5,688,678; 5,661,007; 5,637,480; 5,639,638; 5,658,882; and 5,635,372).

Among the members of the TGF-β superfamily are the bone morphogenetic proteins (BMP). BMPs were initially identified as regulators of cartilage and bone formation. Subsequent work has shown that BMPs, like other TGF-β superfamily members, play a role in many different biological processes including embryogenesis and morphogenesis of a variety of organs and tissues. Additionally, BMPs play a role in the growth, differentiation, and chemotaxis of several different cell types such as hematopoietic cells, epithelial cells, mesenchymal cells, and neuronal cells (Reddi, 1998, *Nature Biotechnology* 16:247; Ebendal, supra).

BMPs, like other members of the TGF-β superfamily are highly conserved across different animal species. The mature human BMP-2, for example, is completely homologous with mouse and rat BMP-2. The biologically active form of BMP-2 is a homodimer consisting of a disulfide linked carboxy terminal domain of 114 amino acids. BMP-2 exerts its affect on target cells by binding to a cell surface receptor comprised of a hetero-oligomer. The receptor is a complex of two serine/threonine kinase receptors (see Ebendal, supra; Reddi supra).

The human homolog of BMP-2 has been cloned, Wozney, 1989, *Prog. Growth Factor Res.* 1(4):267. Recombinant human BMP-2 can be expressed as a fragment of the full length BMP-2 consisting of either amino acids 266–396 or 283–396. The fragments form both homodimers and heterodimers resulting in six different isoforms. The six dimeric isoforms are denoted: <Q283/<Q283, <Q283/Q283, Q283/Q283, <Q283/T266, Q283/T266 and T266/T266 and can be separated by cation exchange chromatography (FIG. 1). The number 283 or 266 refers to the N-terminal amino acid position in the full length rhBMP-2. The letter refers to the amino acid at the N-terminus (i.e. Q or T) and the "<" refers to the cyclization of the glutamine (Q) at position 283 to form pyroglutamic acid. Thus, for example, <Q283/Q283 refers to a rhBMP-2 disulfide linked dimer wherein one monomer of the dimer has the cyclized N-terminal glutamine and the other monomer does not.

rhBMP-2 has several clinical applications which require the regeneration of bone. Thus, rhBMP-2 can be used for spinal fusion to treat degenerative disk disease. rhBMP-2 can also be used to treat long bone fractures. It can also be used to treat individuals requiring artificial teeth who lack sufficient bone mass to support the implants.

Maintaining the solubility of a protein is frequently important either for maintaining bio-availability and/or activity of the protein. Protein solubility is dependent upon a variety of factors. These factors include environmental conditions such as pH, salt concentration, temperature and the chemical characteristics of the solvent, as well as innate properties of the protein of interest, such as the primary amino acid sequence and the structural conformation of the protein. Frequently, bio-medical and/or pharmacological applications involving a protein of interest require environmental conditions which do not optimize the solubility of the protein of interest. Precipitation of the protein is the result, thus limiting bio-availability and/or activity of the protein of interest. Accordingly one aspect of the invention relates to increasing the solubility of a protein of interest, e.g., a member of the TGF-β superfamily, and thereby increasing its bio-availability and/or activity either as a pharmaceutical composition or a research reagent.

The instant invention is based at least in part on the surprising discovery that various peptide fragments of recombinant human BMP-2 (rhBMP-2) increase solubility and/or inhibit precipitation, of a protein, such as, a member of the TGF-β superfamily.

SUMMARY OF THE INVENTION

The invention relates to the discovery that the N-terminus 17 amino acid extension of the T266 isoform of rhBMP-2 and fragments thereof, increase the solubility and/or inhibit precipitation of a protein, such as, rhBMP-2. The invention also relates to the discovery that the N-terminus 17 amino acid extension of the T266 isoform of rhBMP-2 can resolubilize a protein that has precipitated out of solution. Thus, the invention can be used as an excipient to maintain or increase the solubility of a protein of interest in a pharmaceutical composition or in a research reagent. The invention can also be used to resolubilize a protein that has precipitated out of solution.

The invention, therefore, relates to a composition, comprising the N-terminus 17 amino acid extension of the T266 isoform of rhBMP-2, or a fragment thereof, which inhibits the precipitation from a solution, and/or increases the solubility, of a protein of interest. In one embodiment, the protein of interest is a member of the TGF-β superfamily, e.g., BMP-2, TGF-β, BMP-12, BMP-13, BMP-6. In another embodiment, the protein of interest is any one of the rhBMP-2 isoforms, e.g., Q283/<Q283, <Q283/Q283 and Q283/Q283.

The invention further relates to a composition comprising a DNA sequence (SEQ ID NO:2) encoding the N-terminus 17 amino acid extension of the T266 isoform of rhBMP-2, or a fragment thereof, which inhibits the precipitation from a solution, and/or increases the solubility, of a protein of interest.

The invention also relates to a method of inhibiting the precipitation of a protein of interest from solution and/or increasing the solubility of a protein of interest. Said method comprises contacting a protein of interest with a peptide, or a fragment thereof, in an amount sufficient to inhibit precipitation of said protein, compared to said protein that has not been contacted with the peptide or fragment thereof, wherein said peptide comprises Thr-Phe-Gly-His-Asp-Gly-Lys-Gly-His-Pro-Leu-His-Lys-Arg-Glu-Lys-Arg (SEQ ID NO:1). In one particular embodiment, the peptide is encoded by the DNA sequence comprising ACG TTT GGC CAC GAC GGC AAA GGC CAC CCC CTG CAC AAA AGA GAG AAA AGA (SEQ ID NO:2). The protein of interest can be any protein. In one embodiment the protein of interest is a member of the TGF-β superfamily, e.g., BMP-2, TGF-β, BMP-12, BMP-13, BMP-6. In another embodiment, the protein of interest is at least one of the rhBMP-2 isoform subunits consisting of Q283 or <Q283.

Additional objects and advantages of the invention will be set forth in part in the description which follows, and in part will be obvious from the description, or through the practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying figures, which are incorporated in and constitute a part of this specification, and together with the description, serve to explain the principles of the invention.

DESCRIPTION OF THE EMBODIMENTS

Figure 1:
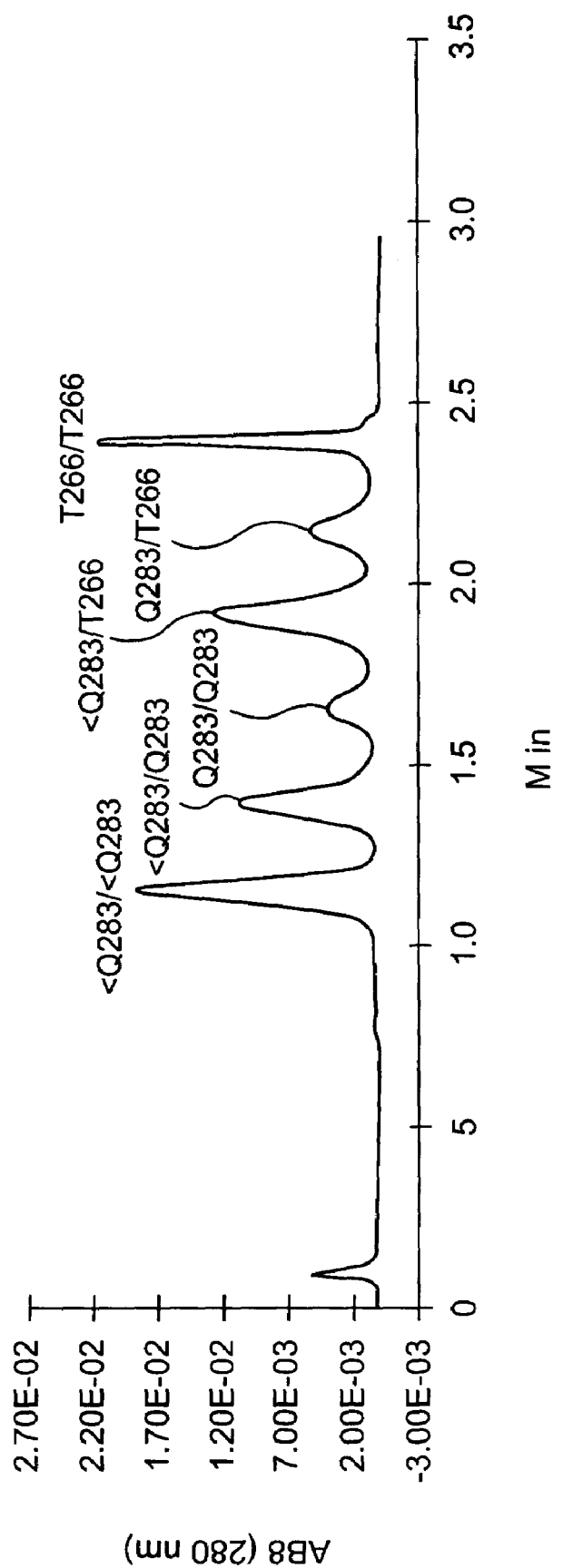
FIG. 1 is a chromatagram showing the elution profile of the six isoforms of rhBMP-2 eluted off a cation exchange column.

"Biologically active," as used herein, means a function or set of activities performed by a molecule in a biological context (i.e. in an organism or an in vitro facsimile thereof). Biological activity can include for example the regulation of cartilage and bone formation or the induction of growth, differentiation, or chemotaxis.

"Operatively linked," as used herein, refers to a functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The invention is based on the surprising discovery that a peptide, derived from rhBMP-2, and fragments thereof, increase the solubility of various isoforms of rhBMP-2. The peptide comprises amino acids 266–282 of rhBMP-2 (SEQ ID NO:1). A fragment is at least 4 amino acids, at least 6 amino acids, at least 8 amino acids, at least 10 amino acids, at least 12 amino acids, at least 14 amino acids, at least 16 amino acids of SEQ ID NO:1. The peptide is also known as the N-terminus 17 amino acid extension of the T266 isoform of rhBMP.

There are six dimeric isoforms of rhBMP-2. The six isoforms include <Q283/<Q283, <Q283/Q283, Q283/Q283, <Q283/T266, Q283/T266 and T266/T266. T266/T266 dimeric isoform is highly soluble in the presence of sodium sulfate, however its bio-activity is limited compared to the other isoforms. The T266/T266 isoform remains solubilized when dialyzed into salt free or low salt buffer, while the dimers that contain either <Q283 or Q283 isoform subunit precipitate during dialysis to remove salt. The Q283 and <Q283 isoform subunits are truncated at amino acid 283 on the N-terminus. The Q283 isoform subunits thus contain amino acids 283–396 of BMP-2 which is the isoform found in vivo. The 283 isoform subunits do not contain the 17 N-terminus amino acid extension, i.e., amino acids 266–282 found on the T266 isoform subunit.

When the 17 amino acid extension is present in the T266 isoform, it confers increased solubility to rhBMP-2. In addition, the 17 amino acid N-terminus of the T266 isoform can resolubilize precipitated isoforms of rhBMP-2. Surprisingly, fragments derived from the 266–282 N-terminus extension of the T266 isoform of rhBMP-2 also confer increased solubility to rhBMP-2 and inhibit precipitation.

Thus, one embodiment of this invention provides methods of increasing the solubility of, inhibiting precipitation of, and resolubilizing the more active forms of rhBMP-2 for use as a pharmaceutical composition or a research reagent. Another embodiment of the invention provides a composition comprising a peptide derived from the T266 isoform of rhBMP, wherein said peptide increases the solubility of a protein of interest, and/or inhibits precipitation of a protein of interest and/or resolubilizies a protein of interest that has precipitated out of solution. In one such embodiment, the composition of the invention comprises the N-terminus 17 amino acid extension of the T266 isoform of rhBMP-2 (SEQ ID NO:1). In another embodiment, the invention comprises a fragment of SEQ ID NO:1, including but not limited to, e.g., amino acids 6–17 of SEQ ID NO:1, amino acids 11–17 of SEQ ID NO:1, or amino acids 14–17 of SEQ ID NO:1. Contacting a protein of interest, with the peptide of SEQ ID NO:1, or fragment thereof, increases the solubility of the protein of interest and/or inhibits the precipitation of the protein of interest and/or resolubilzes the protein of interest after it has precipitated from solution. One of skill in the art would understand that to ascertain that a fragment of SEQ ID NO:1 increases solubility of, or inhibits precipitation of a protein of interest, or resolubilizes a protein of interest, the skilled artisan would compare the solubility of, or precipitation of, or resolubilization of the protein of interest, before and after, or with and without, contacting the protein of interest with the peptide of SEQ ID NO:1, or fragment thereof.

In one embodiment, solubility is defined as having an optical density as measured by a spectrophotometer at a wavelength of 340 nanometers of ≦0.1 when measured in a quartz cuvette with a 1 centimeter pathlength. The spectrophotometer can be for example a Hitachi U-2000.

In one embodiment of the invention, a peptide encoded by SEQ ID NO:1 or a fragment of a peptide encoded by SEQ ID NO:1, when in contact with a protein of interest, results in said protein of interest becoming more soluble and/or less likely to precipitate and/or becoming resolubilized if said protein has already precipitated.

In an alternate embodiment, a peptide encoded by a DNA sequence comprising SEQ ID NO:2 or a fragment of a peptide encoded by a DNA sequence comprising SEQ ID NO:2, when in contact with a protein of interest, results in said protein of interest becoming more soluble and/or less likely to precipitate and/or becoming resolubilized if said protein has already precipitated.

Due to the known degeneracy of the genetic code, wherein more than one codon can encode the same amino acid, a DNA sequence can vary from that shown in SEQ ID NO:2 and, and still encode a polypeptide having the amino acid sequence of SEQ ID NO:1. Such variant DNA sequences can result from silent mutations (e.g., occurring during PCR amplification), or can be the product of deliberate mutagenesis of a native sequence.

The invention thus provides isolated DNA sequences encoding polypeptides of the invention, selected from: (a) DNA comprising the nucleotide sequence of SEQ ID NO:2; (b) DNA encoding the polypeptides of SEQ ID NO:1; (c) DNA capable of hybridizing to a DNA of (a) or (b) under conditions of moderate stringency and which encodes peptides having the functional properties of the peptides of the invention (i.e., increases solubility of a protein of interest or resolubilizes a protein of interest); (d) DNA capable of hybridization to a DNA of (a) or (b) under conditions of high stringency and which encodes peptides having the functional properties of the peptides of the invention, and (e) DNA which is degenerate as a result of the genetic code to a DNA defined in (a), (b), (c), or (d) and which encode peptides having the functional properties of the peptides of the invention. Of course, polypeptides encoded by such DNA sequences are encompassed by the invention.

As used herein, conditions of moderate stringency can be readily determined by those having ordinary skill in the art based on, for example, the length of the DNA. The basic conditions are set forth by Sambrook et al. *Molecular Cloning: A Laboratory Manual*, 2 ed. Vol. 1, pp. 1.101–1.104, Cold Spring Harbor Laboratory Press, (1989), and include use of a prewashing solution for the nitrocellulose filters 5×SSC, 0.5% SDS, 1.0 mM EDTA (PH 8.0), hybridization conditions of about 50% formamide, 6×SSC at about 42° C. (or other similar hybridization solution, such as Stark's solution, in about 50% formamide at about 42° C.), and washing conditions of about 60° C., 0.5×SSC, 0.1% SDS. Conditions of high stringency can also be readily determined by the skilled artisan based on, for example, the length of the DNA. Generally, such conditions are defined as hybridization conditions as above, and with washing at approximately 68° C., 0.2×SSC, 0.1% SDS. The skilled artisan will recognize that the temperature and wash solution salt concentration can be adjusted as necessary according to factors such as the length of the probe.

In another embodiment, the nucleic acid molecules of the invention also comprise nucleotide sequences that are at least 80% identical to SEQ ID NO:2. Also contemplated are embodiments in which a nucleic acid molecule comprises a sequence that is at least 90% identical, at least 95% identical, at least 98% identical, at least 99% identical, or at least 99.9% identical to SEQ ID NO:2.

The percent identity may be determined by visual inspection and mathematical calculation. Alternatively, the percent identity of two nucleic acid sequences can be determined by comparing sequence information using the GAP computer program, version 6.0 described by Devereux et al. (*Nucl. Acids Res.* 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure, National Biomedical Research Foundation*, pp. 353–358, 1979; (2) a penalty of 3.0 for each gap and an additional 0.10 penalty for each symbol in each gap; and (3) no penalty for end gaps. Other programs used by one skilled in the art of sequence comparison may also be used.

The invention also relates to a method of making a protein of interest more soluble or less likely to precipitate from solution, said method comprising genetically engineering said protein by annealing the DNA sequence encoding the N terminus 17 amino acid extension of the T266 isoform of rhBMP (SEQ ID NO:2), or a fragment thereof, to the DNA sequence encoding said protein of interest. Accordingly, in one embodiment the DNA sequence is operatively linked to a DNA sequence encoding a protein of interest. The DNA sequence encoding said protein of interest can be any DNA sequence which when translated produces said protein of interest (e.g. genomic DNA, cDNA). In one embodiment the DNA sequence of the invention (SEQ ID NO:2) or fragment thereof is annealed to the amino (N) terminus of said protein of interest. In another embodiment, the DNA sequence of the invention (SEQ ID NO:2) or a fragment thereof is annealed to the carboxy (C) terminus of said protein of interest. The DNA encoding said protein of interest annealed to SEQ ID NO:2 or a fragment thereof can be engineered into any vector or plasmid known in the art. Expression vectors and cloning vectors are described in, for example, *Cloning Vectors: A Laboratory Manual* (Powells et al. 1985, Supp. 1987) and *Molecular Cloning A Laboratory Manual Second Edition* (Sambrook et al. 1989, Cold Spring Harbor Laboratory Press) Alternatively, the DNA sequence encoding the protein of interest can be amplified using the polymerase chain reaction (PCR) (*Current Protocols in Molecular Biology*, John Wiley and Sons, New York, 1989).

The protein of interest annealed to SEQ ID NO:2 may be produced by transformation or transfection of a suitable host cell with all or part of DNA encoding said protein of interest annealed to SEQ ID NO:2 or a fragment thereof. Those skilled in the art of molecular biology will understand that any of a wide variety of expression systems may be used to express the DNA encoding the protein of interest annealed to SEQ ID NO:2 or a fragment thereof. The precise host cell used is not critical to the invention. Examples of host cells include, but are not limited to prokaryotic cells such as *E. coli* or eukaryotic cells such as COS1, CHO, NIH3T3, *S. Frugiperda*, or *S. cerevisiae*. Such cells are readily available from a wide range of sources (e.g., American Type Culture Collection, Rockland, Md.) The method of transfection and the choice of expression plasmid or vector will depend on the host system selected. Transformation and transfection methods are described, e.g., in Ausubel supra.

The invention also relates to a peptide encoded by SEQ ID NO:1, or a fragment thereof, wherein at least one amino acid within said peptide, or fragment thereof, has been altered by mutation, deletion or substitution with a different amino acid without changing the activity of the peptide, i.e., contacting a protein of interest with said altered peptide still increases the solubility of, or inhibits precipitation of a protein of interest or alternatively resolubilizes a precipitated protein of interest, as compared to said protein not contacted with the peptide encoded by SEQ ID NO:1, or fragment thereof. In another aspect the invention relates to a peptide encoded by SEQ ID NO:1, or a fragment thereof, wherein at least one amino acid as been added onto the C-terminus provided the activity of the peptide or fragment thereof is maintained. In another aspect the invention relates to a peptide encoded by SEQ ID NO:1, or a fragment thereof, wherein at least one amino acid as been added onto the N-terminus provided the activity of the peptide or fragment thereof is maintained. In yet another embodiment the mutation in the peptide, or fragment thereof, results in an amino acid substitution, wherein said substitution is a conservative substitution. A conservative substitution means substituting one amino acid with another amino acid that has similar chemical properties, e.g., polarity, hyrdophobicity, charge. Examples of conservative substitutions include a serine for threonine substitution, or an arginine for lysine substitution, or a valine for alanine substitution. A skilled artisan would understand that many conservative substitutions are possible. In a particular embodiment, the altered peptide is at least 70% identical, 80% identical, 90% identical or 99% identical to the peptide encoded by SEQ ID NO:1.

Any technique for mutagenesis known in the art may be used, to generate mutants of the peptide encoded by SEQ ID NO:1, including inter alia, in vitro site-directed mutagenesis (Hutchinson et al., (1978) *Biol. Chem.* 253:6551; Zoller and Smith, (1984) DNA, 3:479–488; Oliphant et al., (1986) *Gene* 44:177; Hutchinson et al., (1986) *Proc. Natl. Acad. Sci. U.S.A.* 83;710; Huygen et al., (1996) *Nature Medicine*, 2(8):893–898) and use of TAB® linkers (Pharmacia, Peapack, N.J.). PCR techniques may be used for site-directed mutagenesis (Higuchi, 1989, "Using PCR to Engineer DNA", in *PCR Technology: Principles and Applications for DNA Amplification*, H. Erlich, ed., Stockton Press, Chapter 6, pp. 61–70).

The protein of interest can be any protein. In one aspect of the invention the protein of interest is BMP-2, e.g., rhBMP-2. In another aspect, the protein of interest is at least one of the isoform subunits of rhBMP-2, e.g., <Q283 and Q283. The isoform subunits of rhBMP can exist as monomers or as multimers, e.g., dimers. In yet another aspect, the protein of interest is any member of the TGF-β superfamily that shares sequence and/or structural homology to BMP-2, e.g., TGF-β, BMP-12, BMP-6, BMP-13.

The instant invention also provides for a pharmaceutical composition comprising a peptide encoded by SEQ ID NO:1, or a fragment thereof, e.g., amino acids 6–17 of SEQ ID NO:1, amino acids 11–17 of SEQ ID NO:1, or amino acids 14–17 of SEQ ID NO:1, and a biologically active molecule, wherein said peptide encoded by SEQ ID NO:1, or said fragment thereof, increases the solubility of and/or inhibits precipitation of and/or resolubilizes said biologically active molecule and a carrier. In one embodiment the biologically active molecule is a protein or a peptide. Thus, the biologically active molecule can be a member of the TGF-β superfamily, e.g., TGF-β, BMP-12, BMP-6, BMP-13 or derived from a member of the TGF-β superfamily, e.g., a peptide fragment of a TGF-β superfamily member. The protein can be, for example, BMP-2 or rhBMP-2. Alternatively, the protein or peptide can be an isoform subunit of rhBMP-2, e.g., <Q283 and Q283. Said isoform subunit can be a monomer or a multimer, e.g., a dimer. The carrier can be any suitable carrier known in the art. As an example, but not as a limitation, the carrier can be an absorbable collagen sponge (ACS).

The invention relates to a peptide comprising SEQ ID NO:1 or a fragment of SEQ ID NO:1, including, e.g., amino acids 6–17 of SEQ ID NO:1, amino acids 11–17 of SEQ ID NO:1, or amino acids 14–17 of SEQ ID NO:1. Said peptide, or fragment thereof, can be made by any method of peptide synthesis known in the art. As an example, but not as a limitation, solid phase peptide synthesis can be employed to make the composition of the invention. Such methods are described, for example, by Steward and Young (*Solid Phase Peptide Synthesis* (Freeman and Co., San Francisco, 1969).

The peptide encoded by SEQ ID NO:1, or fragment thereof, can be made using recombinant DNA technology. See, e.g., the techniques described in Sambrook et al. 1990, *Molecular Cloning, A Laboratory Manual*, 2d Ed., Cold Spring Harbor Laboratory, Cold Spring Harbor, N.Y. Prokaryotic (e.g. *E. coli*) or eukaryotic cells (e.g. Cos cells, CHO cells) can be used to express the recombinant peptide or fragment thereof, of the invention. Alternatively, an insect system using *Autographa californica* nuclear polyhedrosis virus (AcNPV) can be used to express the peptide, or fragment thereof, of the invention. Recombinant insect virus can be grown in *Spodoptera frugiperda* cells.

The peptide of the invention, or fragment thereof, can be expressed as a fusion protein. Fusion proteins offer the advantages of greater stability and ease of purification of the peptide, or fragment thereof. As an example, but not as limitation, the peptide, or fragment thereof, can be expressed as a GST fusion peptide or a His tagged fusion peptide. Preferably, the fusion tag is cleavable, thus allowing for removal of the tag after the purification step.

The invention also relates to a method of delivering a pharmaceutical composition to a mammal in need of treatment of a disease or a condition. The pharmaceutical composition comprises a biologically active molecule and a peptide comprised of SEQ ID NO:1, or fragment thereof. The method comprises administering the pharmaceutical composition to said mammal to treat said condition. The biologically active molecule can be, for example, any member the TGF-β superfamily or other protein that is rendered more soluble, or resolubilizes, when contacted with a peptide comprised of SEQ ID NO:1, or a fragment thereof, compared to the same protein that is not contacted with a peptide comprised of SEQ ID NO:1, or a fragment thereof. In one embodiment the biologically active molecule is BMP-2 or rhBMP-2.

The method of the invention can be used to treat any condition requiring the administration of a biologically active molecule wherein said biologically active molecule is more soluble when contacted with a peptide comprised of SEQ ID NO:1, or a fragment thereof, than without. The method of the invention can be used to treat any condition requiring the administration of a biologically active molecule wherein said biologically active molecule is resolubilized when contacted with a peptide comprised of SEQ ID NO:1, or a fragment thereof. In one embodiment the condition to be treated requires the regeneration of bone, e.g., spinal fusion or a long bone fracture and the biologically active molecule, i.e., BMP-2 or rhBMP-2 or an isoform subunit of rhBMP-2.

The mammal can be any mammal including, but not limited to, a dog, a cat, a rat, a mouse, a primate, a farm animal such as a cow, a goat, a pig, or a sheep. In one embodiment the mammal is a human.

The method of the invention can be practiced under any bio-chemical and physical conditions that do not interfere with the activity of the SEQ ID NO:1 peptide or fragment thereof. As an example, but not as a limitation the method of invention can be practiced at a temperature of 20° C. and a pH of 4.5 where the peptide is at a concentration of 10–20 fold molar excess of the protein of interest.

Any method known in the art can be used to determine if the method of the invention results in increased solubility of a protein of interest, or results in resolubilization of a protein of interest. As an example, but not as a limitation, measuring the optical density and/or light scattering of the solution containing the protein of interest can be used to determine if the method of the invention increases the solubility of a protein of interest or resolubilizes a protein of interest. Measurements can be taken before and after contacting a protein of interest with a peptide comprised of SEQ ID NO:1 or a fragment thereof.

The method of the invention can be practiced at a temperature in the range >0° C. and <65° C. In one embodiment the method of the invention is practiced at a temperature of 20° C. In another embodiment the method of the invention is practiced at a temperature of 4° C. In yet another embodiment, the method of the invention is practiced at a temperature of 37° C.

The method of the invention can be practiced at any pH so long as the method results in increased solubility of a protein of interest when contacted with a peptide comprised of SEQ ID NO:1, or a fragment thereof, as compared to the solubility of said protein of interest that is not contacted with a peptide comprised of SEQ ID NO:1, or a fragment thereof. Alternatively, the method of the invention can be practiced at a pH that results in the resolubilization of a protein of interest when contacted with a peptide comprised of SEQ ID NO:1, or a fragment thereof. Thus, in one embodiment, the method of the invention can be practiced at a pH between >1 and <7.5. In another embodiment the method of the invention is practiced at physiological pH. In yet another embodiment the invention is practiced at a pH of 4.5.

Any concentration of the peptide comprised of SEQ ID NO:1, or a fragment thereof, can be used in the practice of the methods of the invention so long as the method results in increased solubility of a protein of interest when contacted with a peptide comprised of SEQ ID NO:1, or a fragment thereof, as compared to the solubility of said protein of interest that is not contacted with a peptide comprised of SEQ ID NO:1, or a fragment thereof. Alternatively, any concentration of the peptide comprised of SEQ ID NO:1, or a fragment thereof, can be used in the practice of the methods of the invention so long as the method results in the resolubilization of a precipitated protein of interest when said protein is contacted with a peptide comprised of SEQ ID NO:1, or a fragment thereof. In one embodiment the method of the invention is practiced with a peptide comprised of SEQ ID NO:1, or fragment thereof, at a concentration in the range of 1–1,000 nanomoles. In another embodiment the method of the invention is practiced with a peptide comprised of SEQ ID NO:1, or fragment thereof, at a concentration in the range of 1–1,000 micromoles. In another embodiment the method of the invention is practiced with a peptide comprised of SEQ ID NO:1, or fragment thereof, at a concentration in the range of 1–1,000 millimoles. In another embodiment the method of the invention is practiced with a peptide comprised of SEQ ID NO:1, or fragment thereof, at a concentration in the range of 1–1,000 moles.

The method of the invention involves contacting a protein of interest with a peptide comprised of SEQ ID NO:1, or fragment thereof, wherein said peptide or fragment thereof, increases the solubility of the protein of interest or resolubilizes the protein of interest. In one aspect of the invention, the method of the invention is practiced with a peptide comprised of SEQ ID NO:1, or fragment thereof, that is present at a molar excess compared to the protein of interest. The peptide can be present at a molar excess, compared to the protein of interest, in the range of 1–1000-fold molar excess. In another aspect of the invention the method of the invention is practiced with the protein of interest present at a molar excess compared to the peptide comprised of SEQ ID NO:1, or a fragment thereof. The protein of interest can be present at a molar excess, compared to the peptide comprised of SEQ ID NO:1, or a fragment thereof, in the range of 1–1000-fold molar excess. In one embodiment the method of the invention is practiced with a peptide comprised of SEQ ID NO:1, or fragment thereof, that is present at a 10–20 fold molar excess compared to the protein of interest.

Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. One of skill in the art will appreciate that any numerical value, inherently contains certain errors necessarily resulting from the standard deviation found in their respective testing measurements.

The following examples illustrate, but are not intended to limit, the scope of the invention.

EXAMPLE 1

Solubility of the Six Isoforms of rhBMP-2 rhBMP-2 is produced in Cho cells and contains six dimeric isoforms <Q283/<Q283, Q283/Q283, <Q283/T266, Q283/T266 and T266/T266. The T266 subunit has a 17 amino acid extension on its N-terminus that is lacking in the Q283 and <Q283 subunits. This extension results from the failure of the PACE enzyme to cleave at the C-terminus of $Arg_{282}$ during cellular processing. This occurs because the recombinant protein is overproduced in Cho cells and thus saturates the capacity of the PACE enzyme.

rhBMP-2 has a unique solubility profile. It is most soluble at low salt concentrations and low pH. However, it remains soluble at higher pH values if the salt concentration is increased above an ionic strength of 0.15 M. To determine if any intrinsic solubility differences existed between the different isoforms of rh-BMP2, the isoforms were purified and treated with 5 mM sodium sulfate. The solubility was measured using light scattering at an optical density of 340 nm.

Solubility studies were performed using 5 mM Na2SO4 as a protein precipitating agent. Experiments were performed in 5 mM L-glutamic acid, 5 mM NaCl, 2.5% glycine, 0.5% sucrose, 0.01% (w/v) Polysorbate 80 pH 4.5 at a protein concentration of 0.5 mg/mL and a volume of 0.5 mL. The incubation period was 10 minutes at room temperature for both precipitation and resolubilization of the molecules. The degree of precipitation was measured by light scattering at 340 nm.

Reverse Phase and Cation Exchange Chromatography were performed on supernatant obtained from rhBMP-2 precipitated with 5 mM and 18 mM Na2SO4. The supernatant was separated from the pellet by microcentrifugation at ~14,000 RPM for 30 minutes at about 2° C. to 8° C.

The six dimeric isoforms of rhBMP-2 were separated by cation exchange chromatography (FIG. 1). Incubation of a mixture of all six isoforms of rhBMP-2 with low levels of $Na_2SO_4$ resulted in an increase in optical density indicative of precipitation of the isoforms. The increase in optical density became apparent at about a range of 3 mM to 4 mM $Na_2SO_4$. The amount of precipitated material was determined by reverse phase chromatography by comparing the protein concentration in the starting material with that in the supernatant of the precipitated material. At 5 mM $Na_2SO_4$, the protein concentration had decreased by 63% of the original amount. At 18 mM $Na_2SO_4$ the protein concentration had decreased by 81% of the initial concentration. The supernatants of these precipitates were analyzed by cation exchange chromatography. It was found that the supernatants of the precipitates were enriched for dimers containing the T266 subunit. This initial observation demonstrated a difference in solubility among the six rhBMP-2 isoforms.

Figure 2:
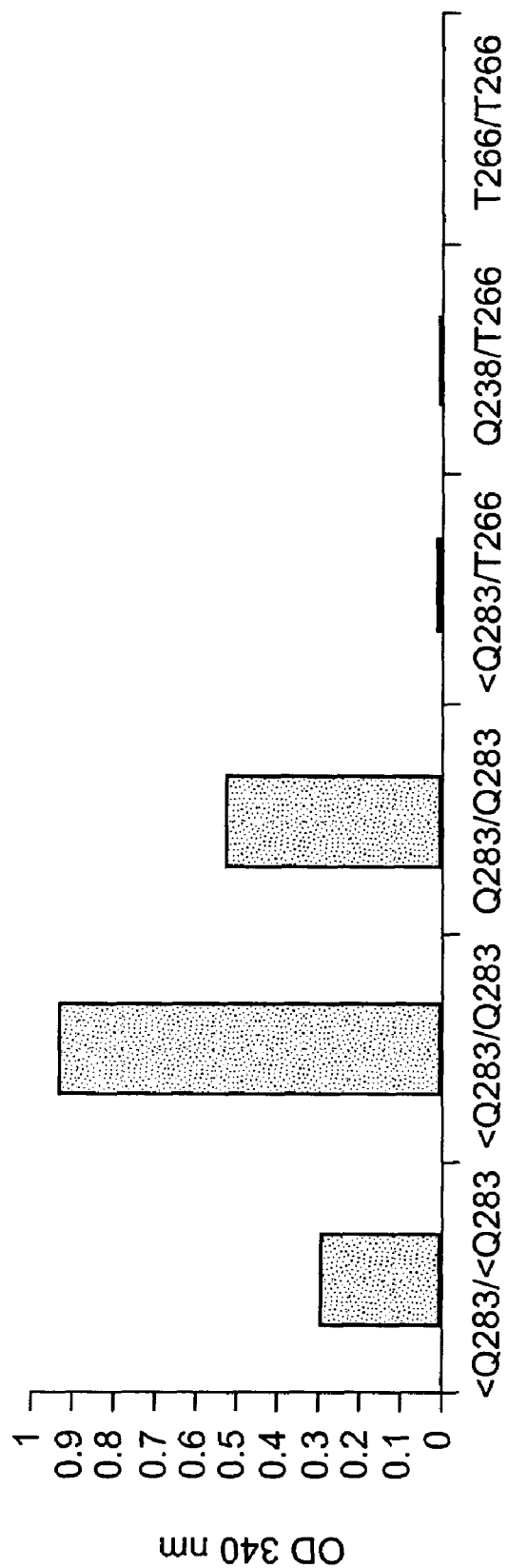
FIG. 2 shows rhBMP-2 isoform solubility in 5 mM sodium sulfate.

To further investigate this phenomena each isoform was purified and incubated with 5 mM $Na_2SO_4$ to better assess their relative solubility. Precipitation of the isoforms was measured by light scattering at 340 nM. All isoforms containing the T266 subunit remained clear after addition of 5 mM $Na_2SO_4$. All isoforms that contained either the Q283 subunit or the <Q283 subunit but not a T266 subunit became opalescent and resulted in an increase of the optical density at 340 nM. This result indicated that the Q283 and <Q283 isoforms precipitated in the presence of 5 mM Na$_2$SO$_4$, while the T266 subunit did not (FIG. 2).

Figure 3:
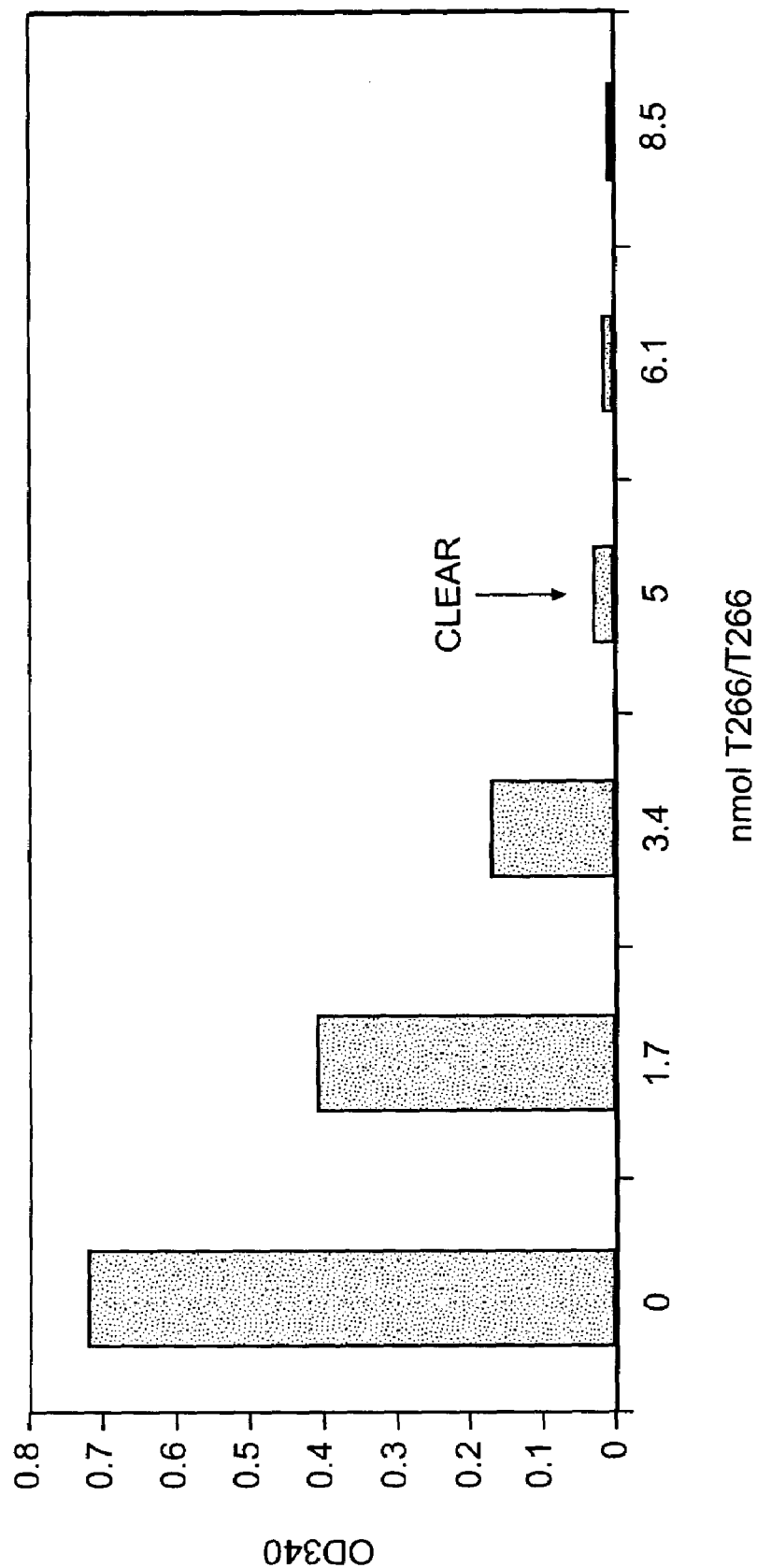
FIG. 3 shows the resolubilization of rhBMP-2 isoform Q283/Q283 with rhBMP-2 isoform T266/T266.
Figure 4:
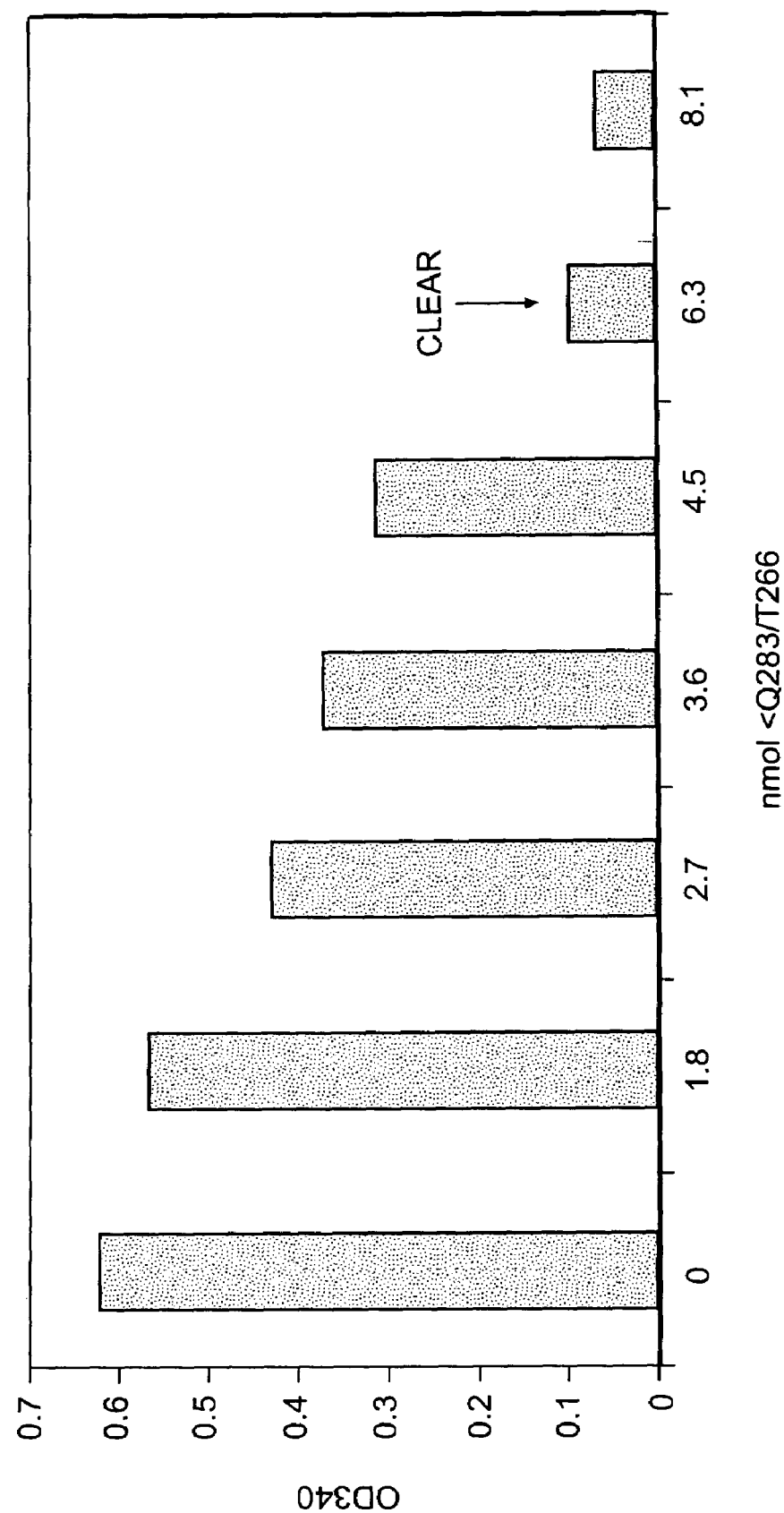
FIG. 4 shows the resolubilization of rhBMP-2 isoform Q283/Q283 with rhBMP-2 isoform <Q283/T266.

The next experiment investigated the ability of the T266/T266 isoform to resolubilize the precipitated Q283/Q283 isoform. Ten nanomoles of Q283/Q283 isoform was precipitated with 5 mM Na$_2$SO$_4$. Varying amounts of the T266/T266 isoform (also in 5 mM Na$_2$SO$_4$) were added to the precipitated Q283/Q283 isoform and the optical density was measured at 340 nM. Addition of the T266/T266 to the precipitated Q283/Q283 isoform resulted in a decrease in the optical density of the solution at 340 nM in a dose dependent manner. Ten nanomoles of Q263/Q263 became clear upon addition of 5 nanomoles of T266/T266. This occurred within ten minutes incubation at room temperature (FIG. 3). Addition of the <Q283/T266 isoform to 10 nanomoles of precipitated Q283/Q283 resulted in a similar decrease in optical density at 340 nM, however higher concentrations of the <Q283/T266 isoform were required to achieve the same effect (FIG. 4).

The difference between the T266 isoform and the Q283 and <Q283 isoforms is the 17 amino acid extension on the N-terminus of the T266 isoform. The next experiment was performed to determine if the 17 amino acid extension, or a fragment thereof, was capable of resolubilizing rhBMP-2. Peptides corresponding to the 17 amino acid N-terminus of the T266 isoform were synthesized and studies were performed to determine if these peptides could resolubilize the mature rhBMP-2.

The following peptides were synthesized: S17: Thr-Phe-Gly-His-Asp-Gly-Lys-Gly-His-Pro-Leu-His-Lys-Arg-Glu-Lys-Arg (SEQ ID NO:1); S12: Gly-Lys-Gly-His-Pro-Leu-His-Lys-Arg-Glu-Lys-Arg (amino acids 6–17 of SEQ ID NO:1); S7: Leu-His-Lys-Arg-Glu-Lys-Arg (amino acids 11–17 of SEQ ID NO:1); Arg-Glu-Lys-Arg (amino acids 14–17 of SEQ ID NO:1).

Figure 5:
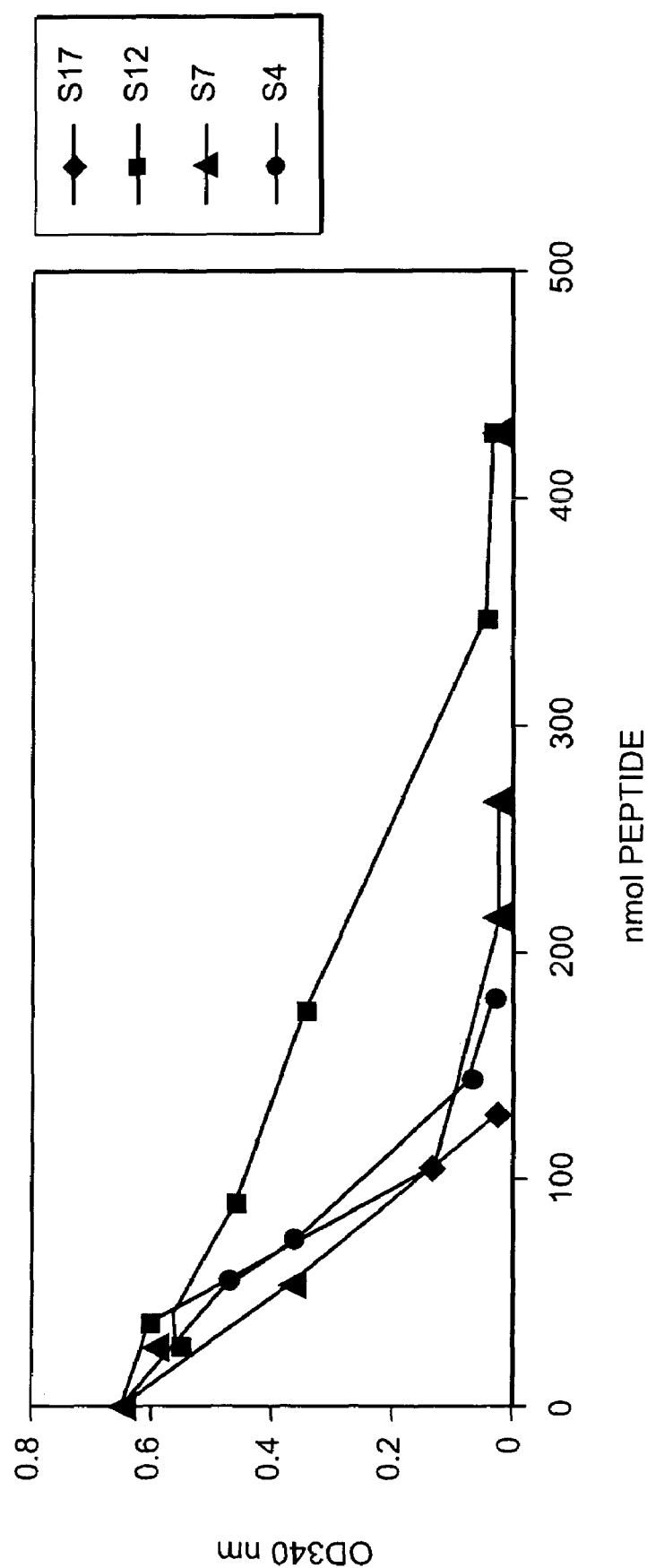
FIG. 5 shows the solubilization of <Q283/<Q283 with synthetic peptides derived from the N-terminus of the extended form (266–396) of rhBMP-2.

All of the synthetic peptides were capable of resolubilizing 10 nanomoles of <Q283/<Q283 that had been precipitated with 5 mM Na$_2$SO$_4$ (FIG. 5). The solubilizing capacity decreased with decreasing chain length. S4, the smallest peptide was still effective at resolubilizing <Q283/<Q283, but required a higher concentration of the peptide.

The ability of the synthetic peptide to resolubilize the <Q283/<Q283 isoform was examined with anions other than sulfate. The peptide was able to resolubilize <Q283/<Q283 precipitated with both sodium chloride and sodium phosphate.

Isoforms of rhBMP-2 that contain the T266 subunit are more soluble than isoforms that contain only the <Q283 or Q283 subunit. The increased solubility, in the presence of various anions is related to the 17 amino acid extension of the T266 subunit.

A peptide comprised of the 17 N-terminus amino acid extension of T266, or a fragment thereof, could be used as an excipient to prevent anion induced precipitation of protein such as rhBMP-2. Because of the high degree of sequence and conformational homology that exists among the members of the TGF-β superfamily the 17 N-terminus amino acid extension of T266, or a fragment thereof, could be used as an excipient or solubilizing agent for any member of the TGF-β superfamily.

The 17 N-terminus amino acid extension of T266 could be used to solubilize or resolubilize or increase solubility of rhBMP-2. Thus, the peptide or fragments thereof could be used to increase solubility of rhBMP-2 in cases where production or purification of the protein results in incomplete anion removal from the protein. It could also be used to solubilize rhBMP-2 protein when it comes in contact with the absorbable collagen sponge (ACS) which is a delivery vehicle for rhBMP-2. The ACS contains uncontrolled levels of multiple anions including sulfate, phosphate and chloride.

EXAMPLE 2

Production of rhBMP-2 with Increased Solubility

A DNA fragment encoding the Q283/Q283 isoform of rhBMP with SEQ ID NO:2 ligated on the N terminus and with flanking BamH1 and Nde1 restriction sites is generated by PCR according to methods known in the art. The PCR product is ligated into the *E. coli* expression vector pT-16b (Novagen). This plasmid is then used to transform *E. coli* JM109. Stimulation of expression of the fusion protein comprising the Q283/Q283 isoform of rhBMP protein with the peptide encoded by SEQ ID NO:2 is achieved by treating the cells with IPTG. The recombinant protein is isolated by metal chelation chromatography according to methods known in the art (e.g. Studier et al. *Methods in Enzymology* 185:60–89, 1990). The fusion protein exhibits increased solubility compared to the Q283/Q283 isoform of rhBMP and is used for example in a pharmaceutical composition.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims and the full range of equivalents to which they are entitled.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A composition comprising a peptide consisting of SEQ ID NO:1 or a fragment thereof, wherein the fragment comprises at least amino acids 14 to 17 of SEQ ID NO:1 and has the ability to increase the solubility of a TGF-β superfamily member protein in solution.

2. The composition of claim 1, wherein said TGF-β superfamily member is BMP-2.

3. The composition of claim 2, wherein said BMP-2 is human BMP-2.

4. The composition of claim 3, wherein said human BMP-2 is rhBMP-2.

5. The composition of claim 4, wherein said rhBMP-2 is an isoform of rhBMP-2.

6. The composition of claim 5, wherein said isoform is chosen from <Q283 or Q283.

7. The composition of claim 6, wherein said isoform is a dimer.

8. The composition of claim 7, wherein said dimer is chosen from <Q283/<Q283, <Q283/Q283 and Q283/Q283.

9. The composition of claim 1, wherein said fragment is selected from the group consisting of amino acids 6–17 of SEQ ID NO: 1, amino acids 11–17 of SEQ ID NO:1, and amino acids 14–17 of SEQ ID NO:1.

10. A pharmaceutical composition comprising a member of the TGF-β superfamily, a peptide consisting of SEQ ID NO:1 or a fragment thereof, wherein the fragment comprises at least amino acids 14 to 17 of SEQ ID NO:1 and has the ability to increase the solubility of a TGF-β superfamily member protein in solution, and a carrier.

11. The pharmaceutical composition of claim 10, wherein said member of the TGF-β superfamily is BMP-2.

12. The pharmaceutical composition of claim 11, wherein said BMP-2 is rhBMP-2.

13. The pharmaceutical composition of claim 12, wherein said rhBMP-2 is an isoform of rhBMP-2.

14. The pharmaceutical composition of claim 13, wherein said isoform is a dimer.

15. The pharmaceutical composition of claim 14, wherein said dimer is selected from the group consisting of <Q283/<Q283, <Q283/Q283 or Q283/Q283.

16. The pharmaceutical composition of claim 10, wherein said carrier is an absorbable collagen sponge.

* * * * *

UNITED STATES PATENT AND TRADEMARK OFFICE
CERTIFICATE OF CORRECTION

PATENT NO.        : 7,241,740 B2                                        Page 1 of 1
APPLICATION NO. : 10/639396
DATED             : July 10, 2007
INVENTOR(S)       : Pilarin E.L. Nichols and Bernardo Perez-Ramirez It is certified that error appears in the above-identified patent and that said Letters Patent is hereby corrected as shown below:

Column 13, line 27, "<Q283 or Q283" should read --<Q283 and Q283--

Column 13, line 31, "<Q283/Q283 and" should read --<Q283/Q283, and--

Column 14, line 30, "<Q283/Q283 or Q283/Q283" should read --<Q283/Q283, and Q283/Q283--

Signed and Sealed this

Twenty-seventh Day of November, 2007

JON W. DUDAS
*Director of the United States Patent and Trademark Office*